(12) United States Patent
Rothschild et al.

(10) Patent No.: US 11,263,893 B2
(45) Date of Patent: Mar. 1, 2022

(54) DEVICES, SYSTEMS, AND METHODS FOR MOBILE PERSONAL EMERGENCY RESPONSE SERVICES

(71) Applicant: Cox Communications, Inc., Atlanta, GA (US)

(72) Inventors: Keith Alan Rothschild, Atlanta, GA (US); Ron Lev, Atlanta, GA (US); Kay Raffi, Atlanta, GA (US); Paul Phipps, Atlanta, GA (US)

(73) Assignee: Cox Communications, Inc., Atlanta, GA (US)

( * ) Notice: Subject to any disclaimer, the term of this patent is extended or adjusted under 35 U.S.C. 154(b) by 0 days.

(21) Appl. No.: 16/928,778

(22) Filed: Jul. 14, 2020

(65) Prior Publication Data

US 2021/0020020 A1    Jan. 21, 2021

Related U.S. Application Data

(60) Provisional application No. 62/874,335, filed on Jul. 15, 2019.

(51) Int. Cl.
| | |
|---|---|
| *G08B 25/01* | (2006.01) |
| *G08B 21/04* | (2006.01) |
| *G06F 1/16* | (2006.01) |
| *A61B 5/11* | (2006.01) |
| *A61B 5/00* | (2006.01) |
| *H04W 4/02* | (2018.01) |

(52) U.S. Cl.
CPC ......... *G08B 25/016* (2013.01); *A61B 5/1112* (2013.01); *A61B 5/1117* (2013.01); *A61B 5/681* (2013.01); *G06F 1/163* (2013.01); *G08B 21/043* (2013.01); *G08B 21/0446* (2013.01); *H04W 4/027* (2013.01)

(58) Field of Classification Search
None
See application file for complete search history.

(56) References Cited

U.S. PATENT DOCUMENTS

2016/0020506 A1* 1/2016 Mahanfar ............... H01Q 9/42
                                                            343/718
2017/0124853 A1* 5/2017 Mehta .................. G08B 25/009

\* cited by examiner

*Primary Examiner* — Adolf Dsouza
(74) *Attorney, Agent, or Firm* — Eversheds Sutherland (US) LLP

(57) ABSTRACT

A wearable device may receive a model from a second device. The model may include an event criterion. The wearable device may determine data indicative of an event associated with a user. The wearable device may determine, based on a comparison of the data to the model, an occurrence of the event. The wearable device may initiate, based on the occurrence of the event, a communication session with a third device.

20 Claims, 10 Drawing Sheets

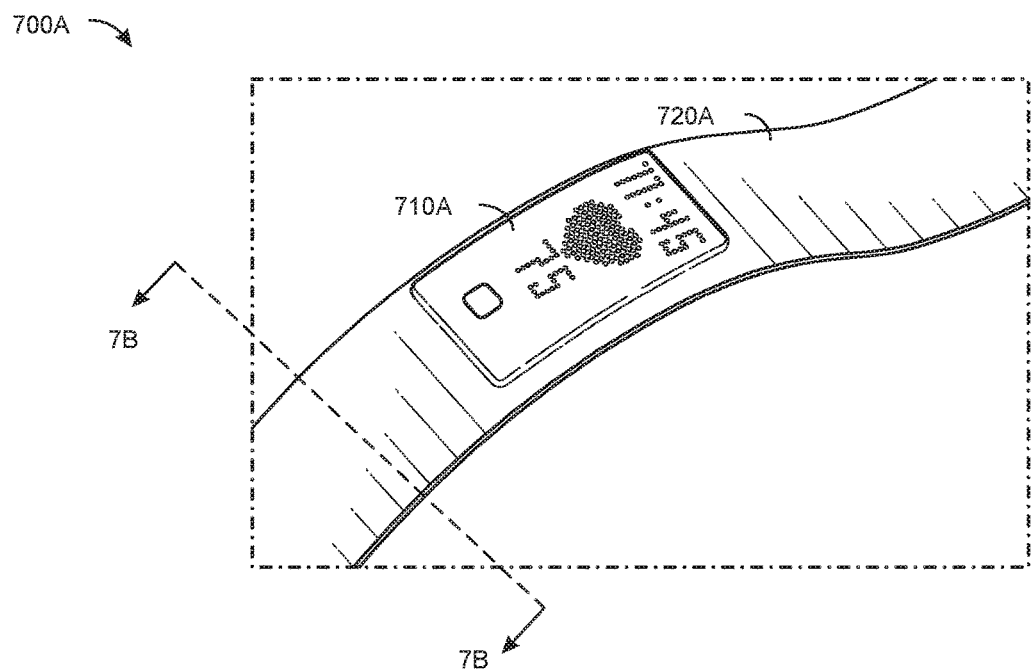
FIG. 7A
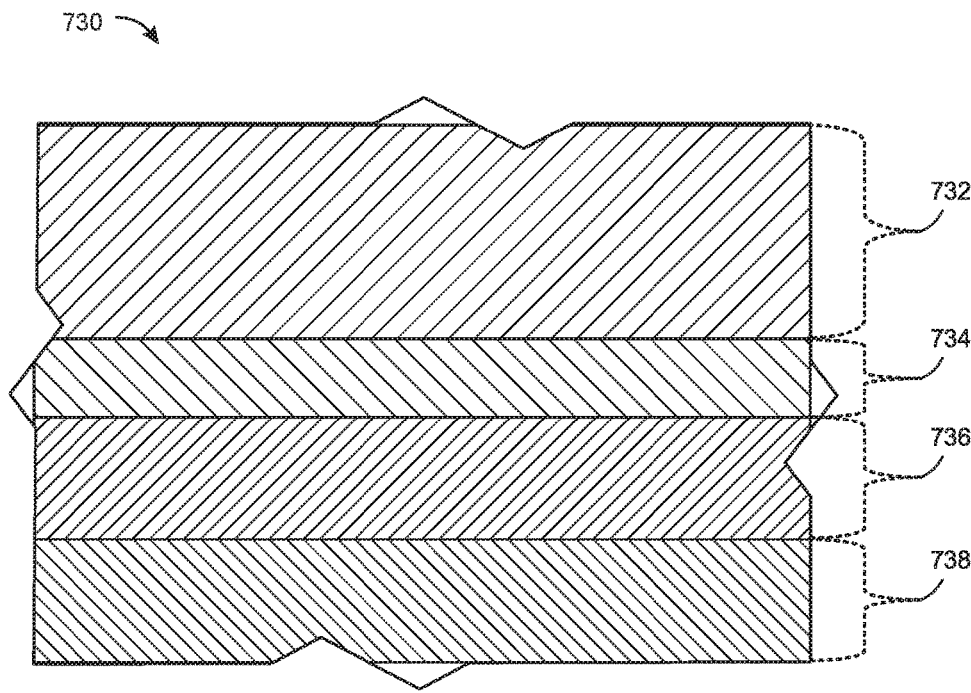
FIG. 7B
FIG. 7A and FIG. 7B

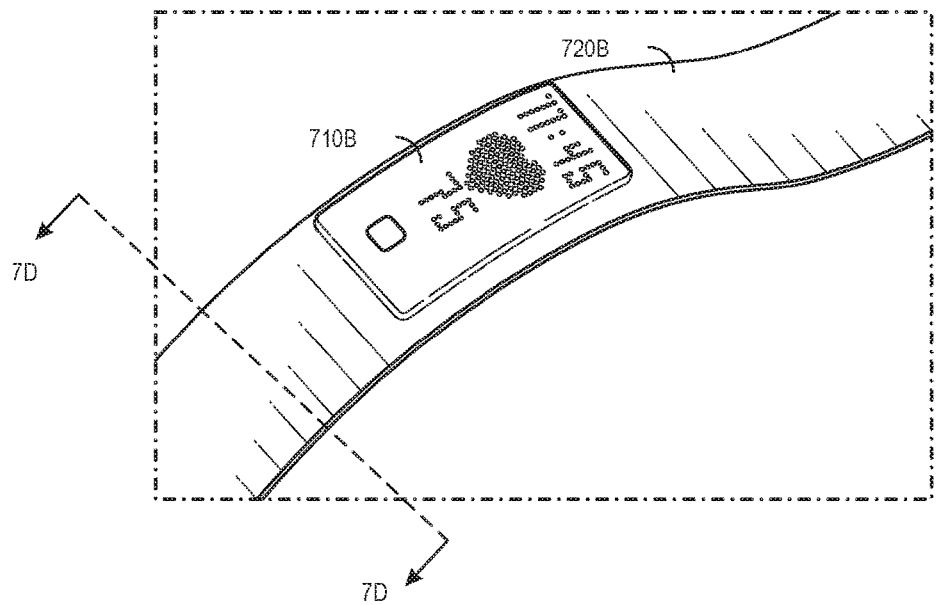
FIG. 7C
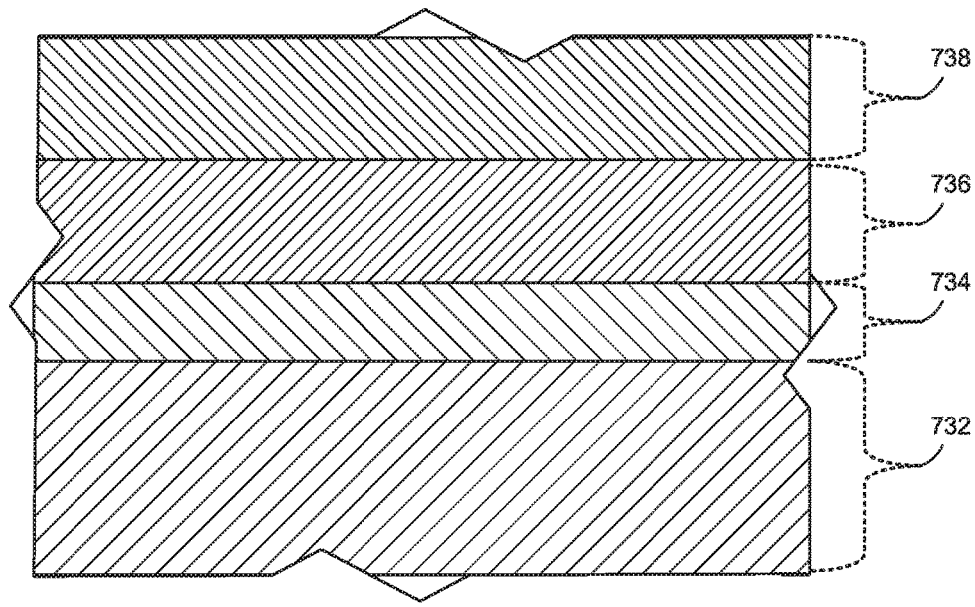
FIG. 7D
FIG. 7C and FIG. 7D

DEVICES, SYSTEMS, AND METHODS FOR MOBILE PERSONAL EMERGENCY RESPONSE SERVICES

CROSS REFERENCE TO RELATED APPLICATIONS

This application claims the benefit of U.S. Provisional Application No. 62/874,335, filed Jul. 15, 2019, which is incorporated by reference in its entirety.

BACKGROUND

Wireless devices are becoming widely prevalent and are increasingly being used for different forms of communication with a variety of devices. However, to conserve resources such as power, some devices rely on other devices to evaluate data and send messages. In some situations, such as medical emergencies, one device's reliance on other devices may result in latency that may undermine user experience. Therefore, there is a need for enhanced systems and methods of communication, and for improved device designs.

BRIEF DESCRIPTION OF THE DRAWINGS

FIG. 7A illustrates an exemplary device for use in mobile personal emergency response services, in accordance with one or more example embodiments of the present disclosure.

FIG. 7B illustrates a cross-section of the device band of the device of FIG. 7A, in accordance with one or more example embodiments of the present disclosure.

FIG. 7C illustrates an exemplary device for use in mobile personal emergency response services, in accordance with one or more example embodiments of the present disclosure.

FIG. 7D illustrates a cross-section of the device band of the device of FIG. 7C, in accordance with one or more example embodiments of the present disclosure.

Figure 1:
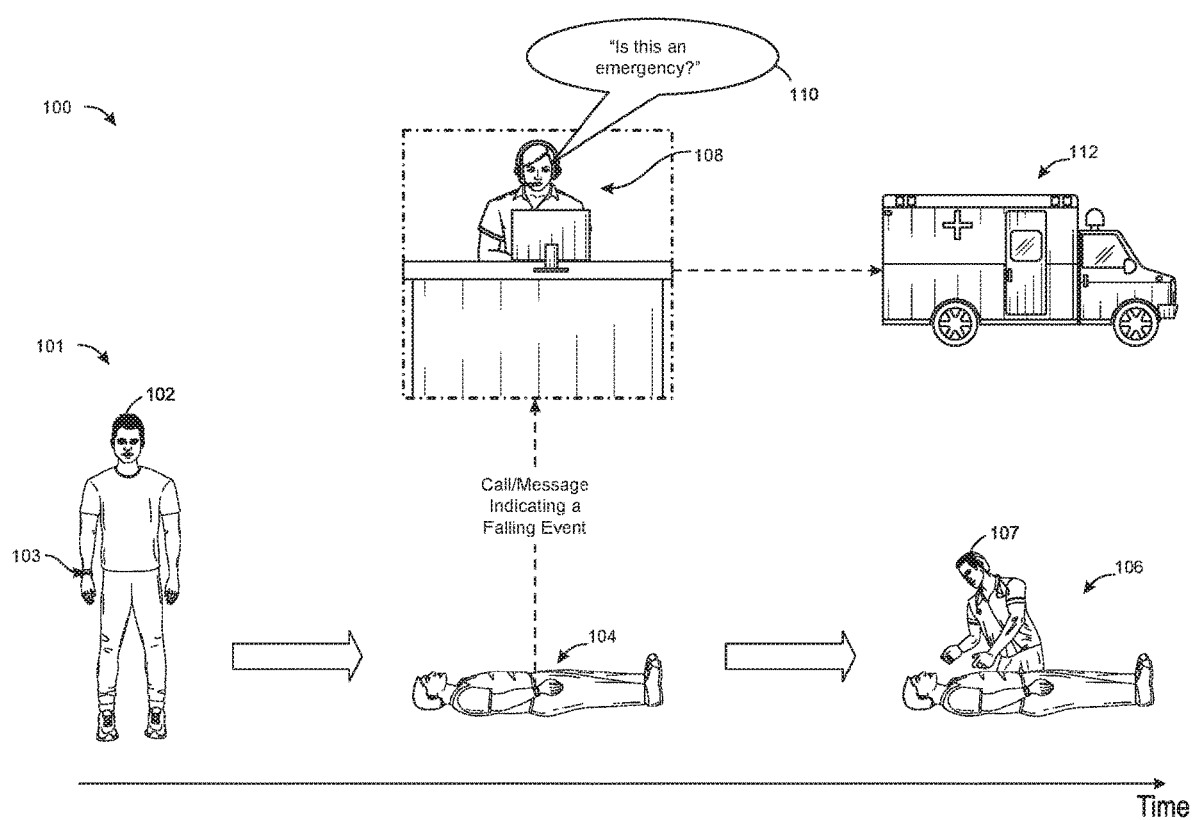
FIG. 1 illustrates an example system for mobile personal emergency response services using devices, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Overview

Example embodiments described herein provide certain systems, methods, and devices for mobile personal emergency response services.

Devices, including wearable devices, may be used to detect events, such as when a person falls or experiences a change in health conditions (e.g., heartrate, blood sugar, electrocardiogram, respiration/oxygenation, and the like), with appropriate user consent and in accordance with applicable laws and regulations. For example, a wearable device such as a watch, band, belt, smart glasses, smart rings, bracelets, or other type of device may facilitate personal emergency response service communications by identifying a condition of the device user, and communicating with other devices to initiate emergency or other services. In particular, some wearable devices rely on other types of devices (e.g., non-wearable devices) to analyze data and to initiate communication sessions, such as phone calls, messages, and the like, on behalf of the wearable devices.

Some devices, such as wearable devices, may be limited in size, thereby limiting physical space for hardware, such as batteries or other power sources. Due to limited battery size, for example, some devices outsource operations, such as calculations and sending of communications, to other devices to conserve the limited power supply (e.g., battery life) of the wearable device. For example, some wearable devices pair with other devices that initiate phone calls and/or perform calculations on behalf of a wearable device. Some wearable devices send data to a network-based (e.g., cloud-based) device for processing. However, outsourcing of calculations and messaging may result in latency/delay as the wearable device waits for another device to perform operations (e.g., delay compared to the wearable device performing an action itself). Relying on another device to perform operations may involve reliance on a connection between devices. In an emergency situation, such as a medical emergency, latency/delay may be the difference between saving a person's life or failing to save a person's life. For example, when a connection between a wearable device and another device is poor or disconnected, life-saving calculations and responses may be delayed or may not occur. Even when a connection between devices is strong, the delay caused by sending data and waiting for another device to initiate communications on behalf of the wearable device may result in costly delays. As such, some devices may benefit from faster calculations and initiations of communications performed by the devices themselves (e.g., rather than outsourcing operations to other devices).

Because the local performance of operations on a battery-powered device may result in a faster use of a battery's power supply, devices that perform operations locally (e.g., in contrast with outsourcing operations to another device) may benefit from maximizing battery size based on size limitations (e.g., a size of wearable watch device). However, even the largest batteries that may fit into a wearable device, such as a smart watch, may require frequent (e.g., daily) charging due to the local performance of operations. As such, some devices may benefit from enhanced designs that allow for more battery power without increasing the size of the devices.

Therefore, devices and device users may benefit from localized event detection and from improved power performance.

In one or more embodiments, a device may identify events, such as medical emergencies, based on local (e.g., on-device) analysis of data associated with a device user. For example, the device may analyze one or more of device data (e.g., accelerometer or other motion data) and biometric data (e.g., heart rate data, blood pressure data, blood glucose data, breathing data, etc.) for the detection of an event such as fall (e.g., the motion data of the device may indicate that a person wearing/holding the device fell down), a cardiac event, or other type of medical emergency. To identify the event locally at the device, the device may compare device and/or biometric data to a model determined by and received from another device (e.g., a cloud-based device or other type of device). The model may provide criteria, such as data thresholds, data profiles, etc., that indicate whether device and/or biometric data is indicative of the occurrence of an event. The device may compare device and/or biometric data to the criteria of the model to determine whether any detected motion and/or biometric data indicates the occurrence of an event.

In one or more embodiments, to respond quickly to a detected event, the device may initiate one or more communications, such as phone calls (e.g., using cellular, Wi-Fi, LTE, etc.), to one or more other devices, such as emergency call centers, medical professionals, family members, caregivers, and the like. For example, the device may have cellular and/or Wi-Fi communication capability to facilitate phone calls executed using the device (e.g., rather than relying on another device, such as a Bluetooth-paired device, to execute the phone call).

In one or more embodiments, to improve the power performance of a watch device that performs event detection locally, at least a portion of the watch device's power supply and/or communication hardware may be housed in the watch band (e.g., instead of within the watch face). For example, one or more batteries and/or antennae may be stored in the band of the watch device, thereby allowing the face of the watch device to store other hardware, and allowing the power supply to be increased (e.g., a larger battery). In one or more embodiments, a combination of one or more power sources, antennas, and/or sensors may be incorporated into a watch band of a watch device (or band of another device securing the device to a person). For example, the band may use a combination of one or more flexible batteries, one or more antennas, and one or more sensors capable of integrating into a link band or various types of strap bands. Such a configuration may allow for a smaller device (e.g., watch face) or other hardware within the watch device, and may improve reception of the antennas (e.g., by using shielding between the battery and antennas). The interchangeability may provide consumers with more options, and the use of some types of bands (e.g., links) may allow for increased power capability (e.g., adding links with more power storage may add to existing power storage of a band).

In one or more embodiments, a watch device with a screen for presenting multiple user interfaces may be interchangeable with the watch band. The size of the screen may be minimized to reduce power consumption and to simplify the device for users. The device may have one or more sensors capable of detecting user data, such as heartrate, device accelerometer data, body and/or device temperature data, device gyroscopic data, electrocardiogram data, and/or other data. The sensors may be in the detachable device and/or in the detachable band. The device may operably connect to the band using one or more connection mechanisms, such as magnets, clasps, adhesives, interconnecting surfaces, and the like. Using sensor data detected by the one or more sensors, the device may detect an event based on comparisons of the sensor data to the model.

In one or more embodiments, the watch device and/or a remote computing network (e.g., cloud network) may perform analysis on data detected by the one or more sensors to determine whether a person has fallen (e.g., based on accelerometer, magnetometer, and/or gyroscope data) and/or whether the person is having an emergency health event (e.g., heart attack, blood sugar incident, hyperventilation, or some other event). For example, the one or more sensors may detect device data and/or biometric data. The device data may detect motion (e.g., translation, rotation, or the like) and/or location information associated with a person wearing the watch device. The biometric data, such as heart rate (HR), breathing rate, pulse oximetry, body fat, hydration level, body temperature, blood sugar, and the like, may provide health information associated with a person. The device data, the biometric data and/or combination thereof may provide indications whether a person preforms normal activities (e.g., sleeping, sedentary, or exercising.) or whether a person is having an emergency event (e.g., a person has fallen and/or is experiencing an emergency health event caused by the falling event, and/or a person is having an emergency health event without falling).

In some embodiments, the device data and biometric data used to identify emergency events may be personalized. For example, thresholds used to determine when an event has occurred and merits an emergency service communication (e.g., a 9-1-1 call) may be customized based on user profile settings and/or historical data. A user profile may indicate a medical history, a user habit, a user preference, or the like. Thresholds indicating an occurrence of an emergency event may be determined based on a user profile and/or based on data from users having similar demographics and/or health profiles. For example, thresholds (e.g., a heart rate threshold, a heart wave threshold, or the like) indicating whether a person is experiencing a heart attack may be set differently for persons who don't have heart diseases and persons who have heart diseases as indicated in respective user profiles. Thresholds indicating whether a person is experiencing an emergency event (e.g., fracture, loss of consciousness, etc.) caused by a falling event may be set differently for young persons and seniors who may have an osteoporosis or other health risks. Additionally and/or alternatively, thresholds indicating whether a person is experiencing an emergency event may be adjusted based on activities (e.g., doing workouts, sleeping, reading, outdoor activities, indoor activities or the like) of a person over a period of time. For example, if a person is doing workouts in a gym, the device may adjust the thresholds, such as increasing a heart rate threshold, a breath rate threshold, a body temperature threshold or the like. If a person is sleeping, the device may adjust the thresholds, such as reducing a heart rate threshold, a breath rate threshold, a body temperature threshold or the like. In some embodiments, thresholds indicating whether a person is experiencing an emergency event may be adjusted based on surrounding environments (e.g., temperatures and/or humidity of surrounding environments). For example, if a person moves from a room with air conditioning to an outdoor location in summer, the device may adjust the thresholds, such as increasing a body temperature threshold or the like. In some embodiments, the device may determine thresholds based on historic data over a predetermined time period, e.g., averaging the historic data, or any other statistical data using the historic data.

In some embodiments, the device may determine an occurrence of an emergency event based on a determination that a change of device data and/or biometric data deviates from/exceeds/fails to exceed a predetermined threshold. For example, the device may determine current data (e.g., current device data and/or biometric data) associated with a person wearing the device. The device may determine historic data (e.g., data obtained last time, average data of the historic data over a predetermined time period, or the like) associated with the person. The device may determine one or more thresholds based on the user profile settings, the historic data, activities associated with the person, surrounding environments, or the like. The device may determine a difference between the current data and historic data. The device may determine that an emergency event occurs when the difference deviates from/exceeds/fails to exceed a predetermined threshold.

In some embodiments, the device and/or the remote computing network may generate one or more machine learning models to determine an occurrence of an emergency event. For example, machine learning models may be trained and learn when data merits emergency services. The device may send device data and/or biometric data captured by sensors to the remote computing network concurrently and/or periodically. The remote computing network may train one or more machine learning models using historic device data and/or biometric data received from the device such that the machine learning models are able to learn when an emergency event occurs. The device may download and store the trained machine learning models from the remote computing network concurrently and/or periodically. The device may use the trained machine learning models to estimate an occurrence of an emergency event based on current and/or new device data and/or biometric data obtained from sensors in substantially real-time without sending the current device data and/or biometric data to the remote computing network. For example, when the device is disconnected with a network (e.g., the device is offline), the device may determine an occurrence of an emergency event based on the stored machine learning models and current device data and/or biometric data. When the device is reconnected with the network (e.g., the device is back online), the device may send the device data and/or biometric data obtained during the disconnection and update the trained machine learning models. Accordingly, due to the omission of training the machine learning models, a computing efficiency of the device is improved. Furthermore, due to the omission of processing on the remote computing network, the device may timely (e.g., substantially real-time) to determine an occurrence of an emergency event.

In some embodiments, demographic data may identify when events justify emergency services based on when users with similar demographic data have received emergency services. For example, most of seniors may have osteoporosis problems and/or other health problems. When the seniors have fallen, the device may determine that the seniors are most likely to have an emergency event (e.g., fracture, faint, or the like) caused by the falling. When young people have fallen, the device may determine that the young people are less likely to have an emergency event (e.g., fracture, faint, or the like) caused by the falling.

In some embodiments, the device may determine an occurrence of an emergency event based on a combination of two or more above methods, e.g., thresholds, machine learning models, and demographic data. For example, the device may determine that a person wearing the device has fallen based on device data by determining that a change of motion and/or location data deviates from/exceeds/fails to exceed a predetermined threshold. The device may utilize machine learning models and/or demographic data to determine that the person is most likely to have an emergency event (e.g., fracture, faint, or the like) caused by the falling. The device may future determine and/or validate that the person has fallen based on the determination that biometric data (e.g., heart rate, breathing rate, pulse oximetry, hydration level, body temperature, blood sugar, and the like) associated with the person deviates from/exceeds/fails to exceed respective predetermined thresholds.

In some embodiments, the device may determine that a person have fallen and/or is having an emergency health event based on a user input. An example user input may include an voice input (e.g., call 911 voice command, make a phone call, voice command for asking for help, or the like), a panic button of the device pressed, or the like. For example, when the device detects an occurrence of an event, the device may send a communication to another device, which may initiate a communication session (e.g., a phone call) with the device, and the person on the other device may request confirmation from the user associated with the event that the event occurred (e.g., a voice confirmation indicating that the person fell, is injured, is having an emergency, etc.). The confirmation or lack thereof (e.g., based on the detected event) may indicate to the other device that the event has occurred, thereby prompting the other device to call an emergency medical professional. When the device detects an event, the device may determine which device to contact and in which manner based on the type of event and/or based on user preferences or device history, and the device may provide information to the other device regarding the type of detected event to facilitate the determination of the proper response (e.g., calling for an ambulance, notifying a medical professional or family member, etc.).

In some embodiments, the device may validate whether a person has fallen based on one or more communications with user devices associated with the person and/or a third party (e.g., friends, relatives, nursing who are close to the person or the like). For example, the device may send a confirmation request (e.g., an audio request, a message request, a call or the like) to the device or other user devices associated with the person and/or user devices associated with the third party. The device may receive a confirmation (e.g., a voice confirmation, text confirmation, or the like). In some embodiments, the device may send a notification/alert and associated data (e.g., device data, biometric data, or the like) to other devices (e.g., a monitoring center, family members, etc.). The other devices may contact and/or dispatch medical professionals, ambulance or the like based on the notification/alert and associated data to provide services for the person who has fallen and/or is having an emergency health event.

In some embodiments, the device may send the associated data (e.g., device data and biometric data) to the remote computing network to refine machine learning models. In some embodiments, the device may not only establish a communication between a person wearing the device and the device, but also establish a communication between the device and a user device (e.g., a mobile phone, smart phone, computer, or the like). For example, a person wearing the device or family members may track activities of the person by downloading an application into their user devices. The device may send device data and biometric data to the user devices, and the user devices may track and analyze activities of the person based on received device data and biometric data, e.g., statistical distribution of the device data and/or biometric data, determining an activity goal for a person, determining whether a person met an activity goal during a predetermined time period, or the like.

In one or more embodiments, a band of the wearable device may refer to a strap or other mechanism used to hold the device or body of a watch or other wearable device to a user's body (e.g., arm, wrist, etc.).

In one or more embodiments, the wearable device may communicate over one or more communication channels and spectrums in a time and/or frequency domain. For example, the wearable device may communicate over cellular communication bands, frequency bands (e.g., 700-970 MHz band or another band), Wi-Fi, Bluetooth, ultrasound, long-term evolution (LTE), and/or other wireless communications.

In one or more embodiments, the wearable device may communicate within the device band and outside of the device band (e.g., using a separate communication channel and/or medium).

In one or more embodiments, the power source of the device may be charged wirelessly (e.g., without physically connecting to a power source). For example, instead of sending wireless data using a wireless protocol such as Wi-Fi or Bluetooth, wireless charging may send power using wireless signals. Antennas may be used to send signals on behalf of the power source, such as probe request or other type of request to find nearby power transmitters. The antennas for the power source of the device may receive wireless power signals from the nearby power source, and may provide the power signals to the power source of the device to charge the power source of the device (e.g., a battery).

In one or more embodiments, the device having a display may be detachable from the watch band. For example, the device may be inserted into an interior of the band. The band may fully or partially cover a display of the device. The band may have material that are semi-transparent or fully transparent to light emitted from the display such that displayed content may be visible to a user though the band. In some embodiments, the device may have the same width as the band. The device may have larger or smaller width than the band. In some embodiments, the device may be taken off from the band for charging.

The above descriptions are for purposes of illustration and are not meant to be limiting. Numerous other examples, configurations, processes, etc., may exist, some of which are described in greater detail below. Example embodiments will now be described with reference to the accompanying figures.

ILLUSTRATIVE PROCESSES AND USE CASES

FIG. 1 illustrates an example system 100 for mobile personal emergency response services using devices, in accordance with one or more example embodiments of the present disclosure. As shown in FIG. 1, at step 101, a person 102 may be wearing a watch device 103. At step 104, the person 102 may fall, and the watch device 103 may detect the fall (e.g., based on motion data of the watch device 103 and/or biometric data of the person 102 detected by the watch device 103). The watch device 103 may detect the failing event at step 104 based on local analysis of motion data associated with the watch device 103 (e.g., by comparing the motion data with one or more thresholds or motion data profiles identified by an event model). Additionally and/or alternatively, the watch device 103 may detect an emergency heath event (e.g., with a cardiac event, or the like) based on local analysis of biometric data associated with the person 102 by comparing the biometric data (e.g., heart rate data, blood pressure data, blood glucose data, breathing data, etc., as sensed by the watch device 103) with one or more thresholds or profiles defined by the event model. The watch device 103 may initiate a communication session (e.g., phone calls using cellar or Wi-Fi, text messages, or the like) with one or more other devices 108, such as an emergency call center device, medical professionals, family members, caregivers, and the like. The watch device 103 may initiate a phone call from the watch device 103 (e.g., using antennae of the watch device 103 rather than relying on a paired device to execute the phone call). For example, the watch device 103 may have cellular and/or Wi-Fi communication capability to facilitate phone calls executed using the device (e.g., rather than relying on another device, such as a Bluetooth-paired device, to execute the phone call). The one or more other devices 108 may receive the communication from the watch device 103, and may respond by sending a query (e.g., a person or automated system may respond with a voice utterance 110, such as "Is this an emergency?") that may be sent to the watch device 103 and presented to the person 102 to allow the person 102 to confirm that an event has occurred. The person 102 may provide a user input (e.g., voice input, a pressed button input, or the like) indicative of the confirmation to the watch device 103, which may provide the confirmation to the one or more other devices 108 (or a lack of response may indicate the occurrence of an event). The one or more other devices 108 may receive the confirmation and may contact a nearby emergency center/medical center to dispatch an ambulance 112 or other personnel to a location where the person 102 is (e.g., based on global positioning data of the watch device 103), or directly dispatch the ambulance 112 to the location. At step 106, a medical professional 107 and/or family members may arrive at the location where the person 102 is to provide emergency assistants for the person 102.

In one or more embodiments, the watch device 103 may identify events, such as medical emergencies, based on local (e.g., on-device) analysis of data associated with the person 102. For example, the watch device 103 may analyze one or more of device data (e.g., accelerometer or other motion data) and biometric data (e.g., heart rate data, blood pressure data, blood glucose data, breathing data, etc.) for the detection of an event such as fall (e.g., the motion data of the device may indicate that a person 102 wearing/holding the watch device 103 fell down), a cardiac event, or other type of medical emergency. To identify the event locally at the watch device 103, the watch device 103 may compare device and/or biometric data to a model determined by and received from another device (e.g., a cloud-based device or other type of device). The model may provide criteria, such as data thresholds, data profiles, etc., that indicate whether device and/or biometric data is indicative of the occurrence of an event. The watch device 103 may compare device and/or biometric data to the criteria of the model to determine whether any detected motion and/or biometric data indicates the occurrence of an event.

In one or more embodiments, to respond quickly to a detected event, the watch device 103 may initiate one or more communications, such as phone calls (e.g., using cellular, Wi-Fi, LTE, etc.), to the one or more other devices 108, such as emergency call centers, medical professionals, family members, caregivers, and the like. For example, the watch device 103 may have cellular and/or Wi-Fi communication capability to facilitate phone calls executed using the watch device 103 (e.g., rather than relying on another device, such as a Bluetooth-paired device, to execute the phone call). The watch device 103 may select the one or more other devices 108 based on preferences of the person 102 and/or the type of event (e.g., fall, cardiac event, respiratory event, etc.).

The watch device 103 and/or the one or more other devices 108 may include any suitable processor-driven device including, but not limited to, a mobile device or a non-mobile, e.g., a static, device. For example, the watch device 103 and/or the one or more other devices 108 may include a user equipment (UE), a station (STA), an access point (AP), a personal computer (PC), a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, an A/V device, a set-top-box (STB), a blu-ray disc (BD) player, a BD recorder, a digital video disc (DVD) player, a high definition (HD) DVD player, a DVD recorder, a HD DVD recorder, a personal video recorder (PVR), a broadcast HD receiver, a video source, an audio source, a video sink, an audio sink, a stereo tuner, a broadcast radio receiver, a flat panel display, a personal media player (PMP), a digital video camera (DVC), a digital audio player, a speaker, an audio receiver, an audio amplifier, a gaming device, a data source, a data sink, a digital still camera (DSC), a media player, a smartphone, a television, a music player, or the like. It is understood that the above is a list of devices. However, other devices, including smart devices, Internet of Things (IoT), such as lamps, climate control, car components, household components, appliances, etc. may also be included in this list.

Figure 2:
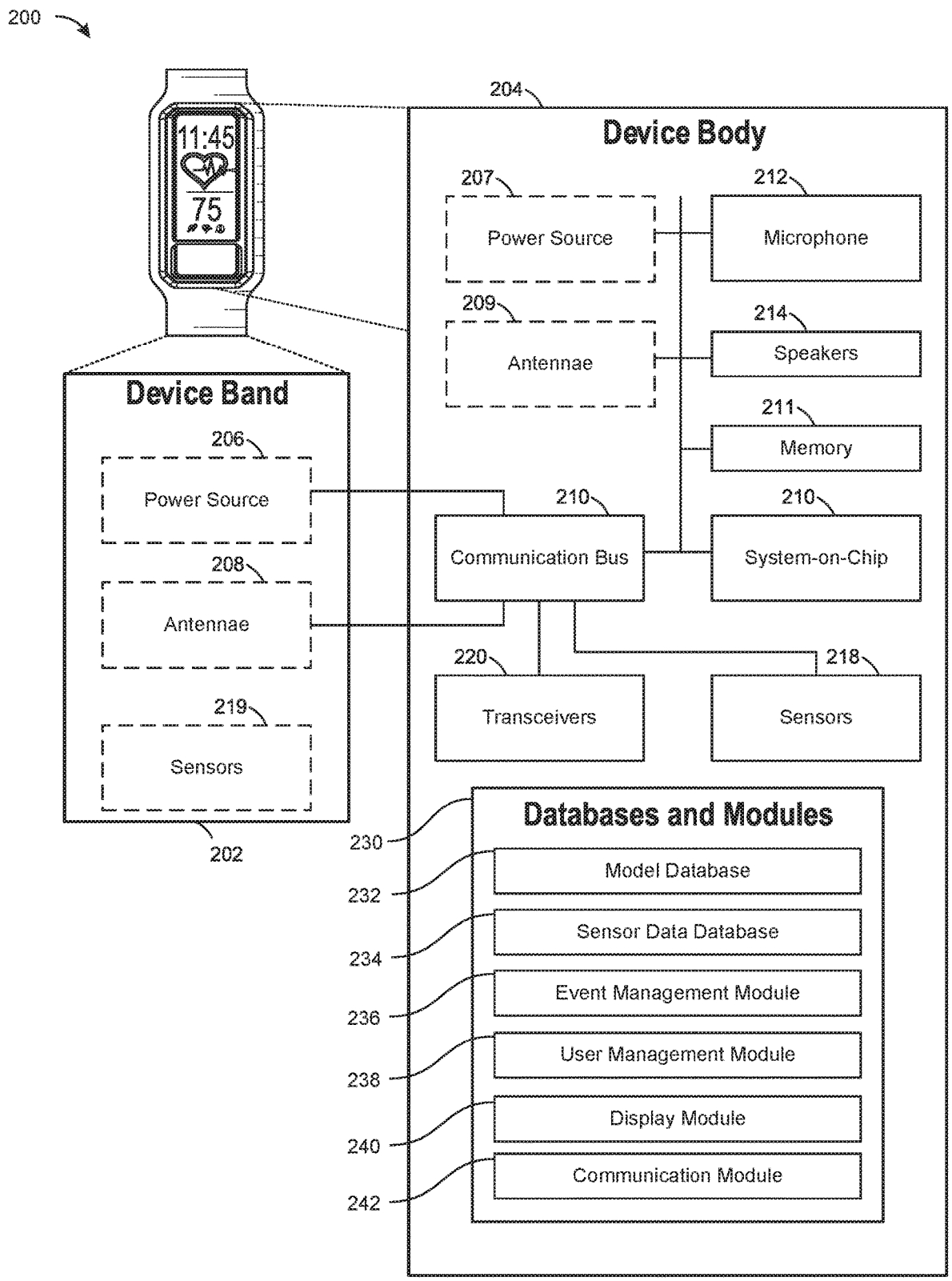
FIG. 2 illustrates a block diagram of a wearable device for use in mobile personal emergency response services, in accordance with one or more example embodiments of the present disclosure.

FIG. 2 illustrates a block diagram of a wearable device 200 for use in mobile personal emergency response services, in accordance with one or more example embodiments of the present disclosure.

Referring to FIG. 2, the wearable device 200 (e.g., similar to the watch device 103 of FIG. 1) may include a device band 202 and a device body 204. The device band 202 may connect to the device body 204, allowing the wearable device 200 to be worn (e.g., by the person 102 of FIG. 1). The device band 202 (e.g., a watch band or other wearable device band or strap) may be operatively in communication with the device body 204 (e.g., a smart watch device or other mobile device). In some embodiments, the device band 202 may include one or more power sources 206 (e.g., batteries) and/or one or more antennae 208 for sending wireless communications. In some embodiments, the device body 204 may include the one or more power sources 206 or other power sources and/or the one or more antennae 208. In some embodiments, some components having an intermediate material may be included between the one or more power sources 206 and the one or more antennae 208. The device band 202 may communicate with the device body 204 using a communication bus 210. The device body 204 may include a microphone 212 or other sound detection device (e.g., capable of voice detection), speakers 214 or other audio/video output device, a system-on-chip 216 or other processing circuitry/hardware, one or more sensors 218 (e.g., temperature sensors, accelerometers, magnetometers, gyroscopes, biometric sensors, etc.), and one or more transceivers 220 (e.g., to communicate wirelessly with other devices and biomedical sensors), one or more power sources 207 (e.g., batteries), and one or more antennae 208. The device body 204 may include memory 211 to store data and/or to store instructions executable by the system-on-chip 216 or other processing hardware. In some embodiments, the one or more sensors 218 may be included in the device band 202 and/or both in the device body 204 (e.g., sensors 219).

The wearable device 200 may detect a fall of a user, a voice command (e.g., a "call 911" command, phone call command, text command, reminder/calendar entry command), a wellness anomaly (e.g. a spike in heartrate), a panic button push or touch, and other events. Voice commands may be sent or translated into text and sent. The wearable device 200 may perform the translation or may rely on another device for translation. The speakers 214 may play audio alerts or voices (e.g., voice calls, reminders to take medication, etc.). For example, the wearable device 200 may be capable of two-way communications between the wearable device 200 and other device (e.g., an emergency service phone or computer). The one or more sensors 218 may detect, using device location (e.g., global navigation satellite system data or more localized data using Wi-Fi, Bluetooth, ultrasound, etc.), that the wearable device 200 has passed a geographic boundary (e.g., a geo fencing), and the wearable device 200 may send alerts when location, orientation, or biomedical data meet criteria (e.g., exceed or fall below threshold values). The alerts may be presented using the wearable device 200 and/or may include alerting other devices regarding the status of the user or the wearable device 200 (e.g., an alert indicating that an event, such as a fall or biomedical event, has occurred). The one or more sensors 218 may detect motion data and/or biometric data that the wearable device 200 may analyze to detect the occurrence of an event (e.g., the falling event of FIG. 1).

In one or more embodiments, having the one or more power sources 206, the one or more antennae 208, and/or the one or more sensors 219 in the device band 202, the size of the device body 204 may be reduced and/or the device body 204 may be used for other hardware.

In one or more embodiments, the one or more power sources 206 and/or the one or more power sources 207 may be chargeable using wireless charging in which the one or more antennae 208 and/or the one or more antennae 209 may receive wireless power signals for the one or more power sources 206 and/or the one or more power sources 207. In this manner, the device body 204 may be charged by the device band 202 even while a user (e.g., the person 102 of FIG. 1) is wearing the device body 204 and the device band 202 (e.g., in the form of the wearable device 200), or while the wearable device 200 is nearby the user (e.g., on a bedside table while the user is sleeping). The one or more antennae 208 and/or the one or more antennae 209 may request and receive wireless power signals, and the wireless power signals may be sent to the one or more power sources 206 and/or the one or more power sources 207 to charge the one or more power sources 206 and/or the one or more power sources 207. The one or more power sources 206 and/or the one or more power sources 207 may supply power to the one or more antennae 208 and/or the one or more antennae 209, and to the device body 204.

In one or more embodiments, the one or more sensors 218 may include motion and position sensors configured to detect device data (e.g., motion data, location data, or the like), and biometric sensors configured to detect biometric data (e.g., heart rate data, blood pressure data, blood glucose data, breathing data, etc.). Examples of motion and positon sensors may include an accelerometer, a magnetometer, a gyroscope, a proximity sensor, a camera, and any sensors configured to detect motions (e.g., rotations, translations, or the like) and/or positions associated with a user wearing the wearable device 200. Example of a biometric sensor may include a heart rate sensor, a breath rate sensor, a blood pressure sensor, or any sensor configured to collect measurable biological characteristics (biometric signals) from a user wearing the wearable device 200.

As shown in FIG. 2, the device body 204 may include databases and modules 230, such as a model database 232, a sensor data database 234, an event management module 236, a user management module 238, a display module 240, and a communication module 242.

The event management module 236 may perform analysis on data detected by the one or more sensors 218 and stored in the sensor data database 234 to determine an occurrence of an event (e.g., whether a person has fallen based on accelerometer, magnetometer, and/or gyroscope data, and/or whether the person is having an emergency health event, e.g., heart attack, blood sugar incident, hyperventilation, or some other event). In some embodiments, the event management module 236 may determine an occurrence of an emergency event based on a determination that a change of device data and/or biometric data deviates from/exceeds/ fails to exceed a predetermined threshold. In some embodiments, the predetermined thresholds may be personalized. For example, thresholds used to determine when an event has occurred and merits an emergency service communication (e.g., a 9-1-1 call) may be customized based on user profile settings and/or historic data associated with the sensor data, historic events and associated data. A user profile generated by the user management module 238 may indicate a medical history, a user habit, a user preference, or the like. For example, the event management module 236 may determine current data (e.g., current device data and/or biometric data) associated with a person wearing the wearable device 200. The event management module 236 may determine historic data (e.g., data obtained last time, average data of the historic data over a predetermined time period, or the like) associated with the person. The event management module 236 may determine one or more thresholds based on the user profile settings, the historic data, activities associated with the person, surrounding environments, or the like. The event management module 236 may determine a difference between the current data and historic data. The device may determine that an emergency event occurs when the difference deviates from/exceeds/fails to exceed a predetermined threshold.

Figure 3:
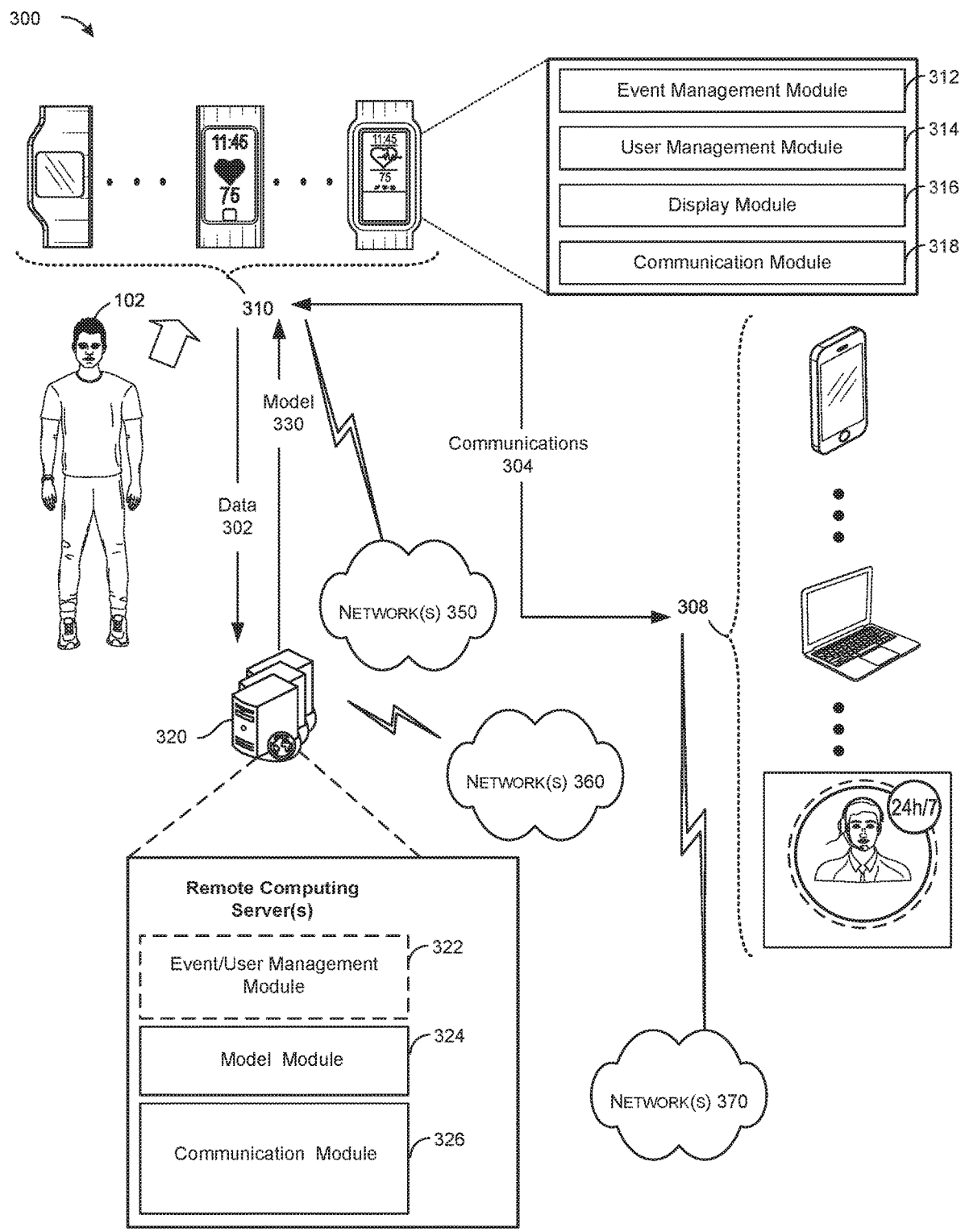
FIG. 3 illustrates an example system for enabling emergency response services, in accordance with one or more example embodiments of the present disclosure.

In some embodiments, the event management module 236 may generate one or more machine learning models to determine an occurrence of an emergency event. Alternatively, the event management module 236 may customize event detection models received from another device (e.g., as explained further with respect to FIG. 3). For example, machine learning models may be trained and learn when data merits emergency services. In some embodiments, the event management module 236 may send device data and/or biometric data captured by sensors 218 to a remote computing network (e.g., a cloud-based device as shown in FIG. 3) concurrently and/or periodically. The remote computing network may train one or more machine learning models using historic device data and/or biometric data received from the wearable device 200 such that the machine learning models are able to learn when an emergency event occurs. The event management module 236 may download and store the trained machine learning models in the model database 232 from the remote computing network concurrently and/or periodically. The event management module 236 may use the trained machine learning models to estimate an occurrence of an emergency event based on current and/or new device data and/or biometric data obtained from the sensors in substantially real-time without sending the current device data and/or biometric data to the remote computing network. For example, when the wearable device 200 is disconnected with a network (e.g., the device is offline), the event management module 236 may determine an occurrence of an emergency event based on the stored machine learning models and current device data and/or biometric data. When the wearable device 200 is reconnected with the network (e.g., the device is back online), the event management module 236 may send the device data and/or biometric data obtained during the disconnection and update the trained machine learning models.

Figure 4:
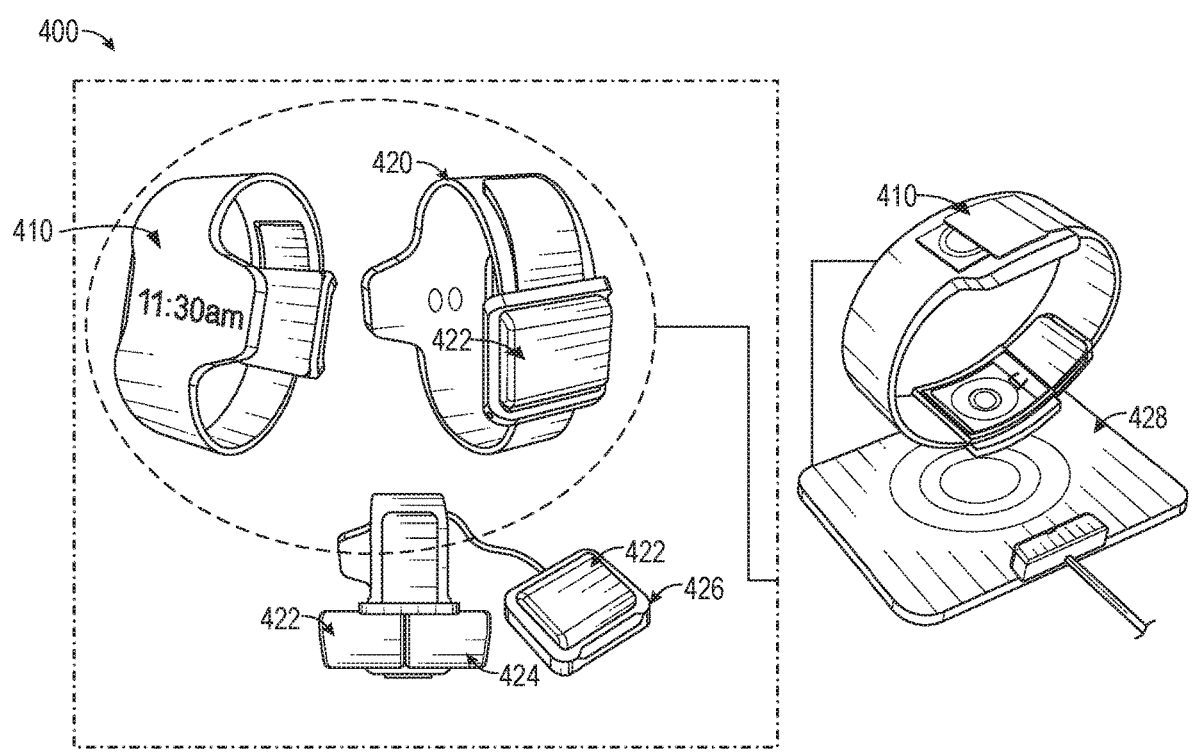
FIG. 4 illustrates a functional diagram of an exemplary device for use in mobile personal emergency response services, in accordance with one or more example embodiments of the present disclosure.
Figure 5:
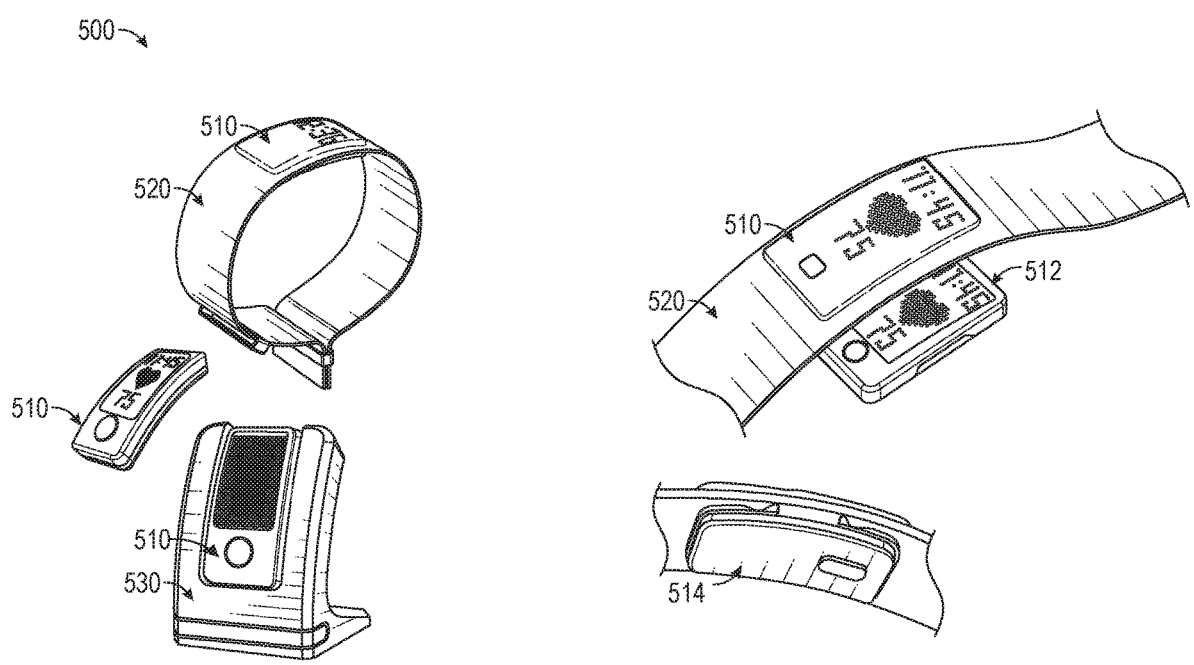
FIG. 5 illustrates a functional diagram of an exemplary device for use in mobile personal emergency response services, in accordance with one or more example embodiments of the present disclosure.
Figure 6:
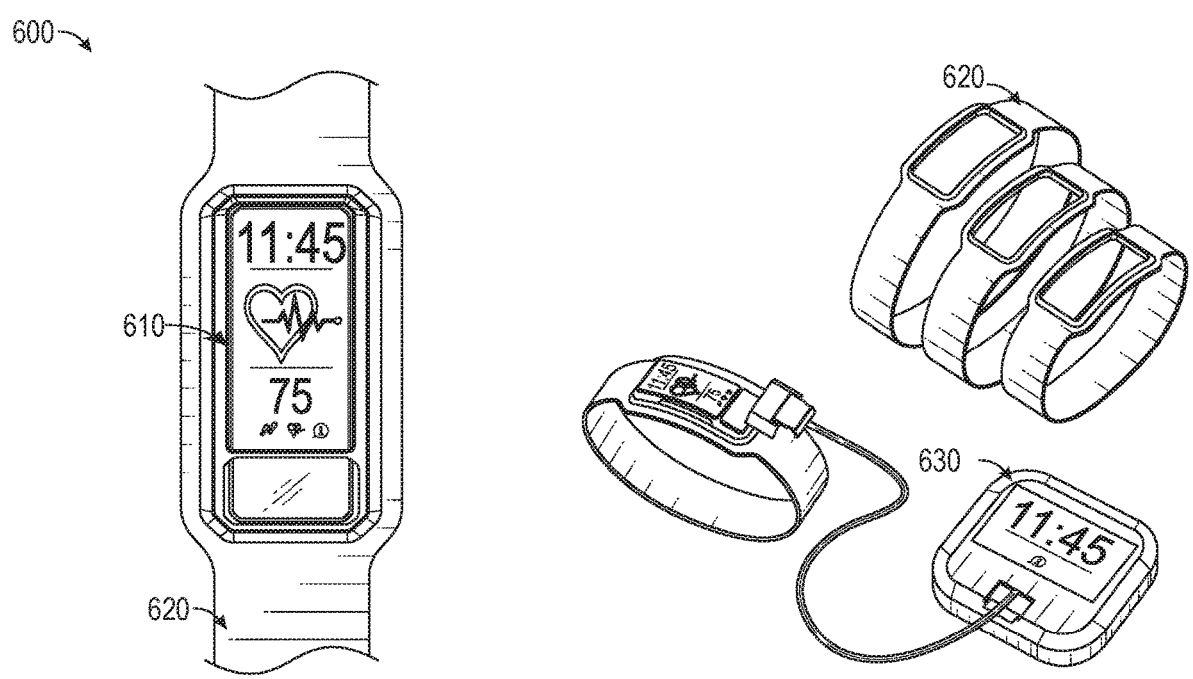
FIG. 6 illustrates a functional diagram of an exemplary device for use in mobile personal emergency response services, in accordance with one or more example embodiments of the present disclosure.

The display module 240 may may generate one or more user interfaces and present the user interfaces via a display screen (e.g., as shown in FIGS. 4-6). The size of the screen may be minimized to reduce power consumption and to simplify the wearable device 200. The display may present the time, date, weather, and information about the user (e.g., biometric data and/or device).

The communication module 242 may establish communications between a user wearing the wearable device 200 and other devices. In some embodiments, the communication module 242 may initiate a communication session, such as phone calls (e.g., using cellular or Wi-Fi), to one or more other devices, such as emergency call centers, medical professionals, family members, caregivers, and the like. For example, the communication module 242 may have cellular and/or Wi-Fi communication capability to facilitate phone calls executed using the wearable device 200 (e.g., rather than relying on another device, such as a Bluetooth-paired device, to execute the phone call). In some embodiments, the communication module 242 may receive an user input (e.g., call 911 voice command, make a phone call, voice command for asking for help, a panic button of the device pressed, or the like) and provide the user input to the event management module 236 to determine an occurrence of an event. In some embodiments, the communication module 242 may provide a voice confirmation indicating that the person fell, is injured, and/or is having an emergency in response to a confirmation request from other devices. The confirmation or lack thereof (e.g., based on the detected event) may indicate to the other device that the event has occurred, thereby prompting the other device to call an emergency medical professional.

The device band 202 and/or the device body 204 may be capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

A storage device (e.g., the model database 232 and/or the sensor data database 234) of the device band 202 and/or the device body 204 may include a machine readable medium on which is stored one or more sets of data structures or instructions (e.g., software) embodying or utilized by any one or more of the techniques or functions described herein. The instructions may also reside, completely or at least partially, within a main memory, within a static memory, or within the hardware processor during execution thereof by the device band 202 and/or the device body 204. In an example, one or any combination of the hardware processor, the main memory, the static memory, or the storage device may constitute machine-readable media.

The term "machine-readable medium" may include a single medium or multiple media (e.g., a centralized or distributed database, and/or associated caches and servers) configured to store one or more instructions.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the device band 202 and/or the device body 204 and that cause the device band 202 and/or the device body 204 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

Instructions may further be transmitted or received over a communications network using a transmission medium via the network interface device/transceiver utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver may include one or more physical jacks (e.g., Ethernet, coaxial, or phone jacks) or one or more antennas to connect to a communications network. In an example, the network interface device/transceiver may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the device band 202 and/or the device body 204 and includes digital or analog communications signals or other intangible media to facilitate communication of such software.

FIG. 3 illustrates an example system 300 for enabling emergency response services, in accordance with one or more example embodiments of the present disclosure.

Referring to FIG. 3, the system 300 may include one or more devices 310 (e.g., the wearable device 200 of FIG. 2) in communication with a remote computing server 320 (e.g., a cloud-based network with one or more servers). The remote computing server 320 may be geographically remote from the one or more devices 310 (e.g., separate devices in different physical/virtual locations).

In one or more embodiments, the one or more devices 310 may include an event management module 312, a user management module 314, a display module 316, and a commutation module 318. The modules of the one or more devices 310 may be an embodiment of the event management module 236, the user management module 238, the display module 240, and the communication module 242 in FIG. 2, and may have similar structure and functions to the respective modules in FIG. 2. The one or more devices 310 may send data 302 to the remote computing server 320. The data 302 may include historic and current device data and/or biometric data, one or more indications of events associated with the above data, or the like. If the event management module 312 determines an occurrence of an event, the event management module 312 may initiate one or more communications 304 with one or more devices 308 for assistance. For example, the one or more communications 304 may include voice calls (e.g., using cellular technology, Wi-Fi, LTE, etc.), messages, and the like. The one or more communications 304 may identify the type of event (e.g., as defined by the event detection model 330) and/or some of the data 302 (e.g., to allow the one or more devices 308 and/or users of the one or more devices 308 to identify the possible event and respond appropriately). As referred to herein, the one or more communications 304 may be communications sessions, such as cellular or Wi-Fi telecommunications, text message or other message sessions, and the like between two or more devices, such as the one or more devices 310 and the one or more devices 308. In this manner, the one or more devices 310 may initiate communication sessions with the one or more devices 308 by executing operations to place a phone call, send a message, and/or request a connection between the devices.

The one or more devices 308 may be devices used by emergency call centers, medical professionals, family members, caregivers, or the like, such as, but not limited to, mobile, desktop, and/or cloud computing devices, such as servers. When an emergency notification via the one or more communications 304 is received by the computing devices 308, the one or more devices 308 may request confirmation (e.g., using the one or more communications 304) from the person 102 (e.g., a user of the one or more devices 310) that the detected event occurred (e.g., a voice confirmation indicating that the person 102 fell, is injured, is having an emergency, etc.). The one or more devices 308 may receive a confirmation (e.g., a voice confirmation, text confirmation, or the like), using the one or more communications 304, and computing devices 308 may contact and/or dispatch medical professionals, ambulance or the like based on the notification/alert and associated data to provide services for the person 102 who has fallen and/or is having an emergency health event.

The remote computing server 320 may communicate with the one or more devices 310 and the one or more devices 308. The remote computing server 320 may be one or more remote cloud-based on computers/servers, and/or network-based on computers/servers. The remote computing server 320 may include an event/user management module 322 (optionally), a model module 324, and a communication module 326.

In some embodiments, the event/user management module 322 may perform similar functions to the event management module 236 of FIG. 2. In some embodiments, the event/user management module 322 may track and analyze activities of the person 102 based on received device data and biometric data. The event/user management module 322 may provide inputs and/or outputs to the one or more devices 308 for presentation and/or future analysis via the communication module 326.

The model module 324 may generate one or more event detection models (e.g., machine learning models) configured to identify an occurrence of an emergency event based on the data 302. For example, machine learning models may be trained and learn when data merits emergency services. The model module 324 may train one or more machine learning models using historic device data and/or biometric data received from the device 310 such that the machine learning models are able to learn when an emergency event occurs. The model module 324 may send an event detection model 330 (e.g., based on the machine learning) to the event management module 312 via the communication module 326. In some embodiments, the model module 324 may utilize the data 302 to refine the event detection model 330. The event detection model 330 may define the criteria that the one or more devices 310 may use to detect an event. The remote computing server 320 may send the event detection model 330 to the one or more devices 310, and may update and send new models to the one or more devices 310 (e.g., based on feedback received by the one or more devices 310, such as whether an event detection model properly identified an event based on the data 302). For example, the event detection model 330 may define data profiles and/or thresholds, such as motion data profiles that indicate whether a device has moved an amount within a certain amount of time, whether biometric data exceeds or fails to exceed biometric thresholds, and the like. In particular, a heart rate above a threshold or below another threshold may indicate an emergency event. A blood glucose level above or below a respective threshold may indicate an emergency event. A blood pressure above or below a respective threshold may indicate an emergency event. An amount and/or type of device motion may indicate that the person 102 fell. The event detection model 330 may account for multiple types of data, time of day, user inputs, etc. For example, the data 302 may satisfy criteria indicative of the occurrence of an event, but based on data indicating that the person 102 is asleep (e.g., based on heart rate data, breathing data, etc.), the event detection model 330 may be used by the one or more devices 310 to determine that an event may not be occurring. In this manner, the event detection model 330 may require that multiple conditions are met by multiple types of data to identify the occurrence of an event.

In one or more embodiments, the one or more devices 310 may communicate using one or more communications networks 350. The remote computing server 320 may communicate using one or more communications networks 360. The one or more devices 308 may communicate using one or more communications networks 370. The one or more communications networks 350, the one or more communications networks 360, and/or the one or more communications networks 370 may include, but not limited to, any one of a combination of different types of suitable communications networks such as, for example, broadcasting networks, cable networks, public networks (e.g., the Internet), private networks, wireless networks, cellular networks, or any other suitable private and/or public networks. Further, any of the one or more communications networks 350, the one or more communications networks 360, and/or the one or more communications networks 370 may have any suitable communication range associated therewith and may include, for example, global networks (e.g., the Internet), metropolitan area networks (MANs), wide area networks (WANs), local area networks (LANs), or personal area networks (PANs). In addition, any of the one or more communications networks may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, white space communication mediums, ultra-high frequency communication mediums, satellite communication mediums, or any combination thereof.

FIG. 4 illustrates a functional diagram of an exemplary device 400 for use in mobile personal emergency response services, in accordance with one or more example embodiments of the present disclosure.

Referring to FIG. 4, the device 400 (e.g., similar to the wearable device 200 of FIG. 2) may include a device body 410 (e.g., having features of the device body 204 of FIG. 2) and a device band 420 (e.g., having features of the device band 202 of FIG. 2). The device band may have a battery 422. The battery 422 may be replaced by a battery 424 via seamless battery swapping without power disengage. The battery 422 may be removed and placed in contact with or near a charger 426 for charging. Additionally and/or alternatively, the device 400 may be charged wirelessly via a wireless charger 428. During wireless charging, instead of removing the battery 422 from the device band 420, the entire device 400 may be charged without contacting the wireless charger 428. The device body 410 may be further away from the wireless charger 428, but the battery 422 may be closer to the wireless charger 428 with facing toward the wireless charger 428.

FIG. 5 illustrates a functional diagram of an exemplary device 500 for use in mobile personal emergency response services, in accordance with one or more example embodiments of the present disclosure.

Referring to FIG. 5, the device 500 (e.g., similar to the wearable device 200 of FIG. 2) may include a device body 510 (e.g., having features of the device body 204 of FIG. 2) and a device band 520 (e.g., having features of the device band 202 of FIG. 2). The device body 510 having a front surface 512 and a back surface 514 may be detachable from the device band 520. The device body 510 may be removed from the device band 520 and may be placed to contact a charger 530 for charging. The device body 510 may be inserted into a portion of an interior of the device band 520. The device band 520 may fully or partially cover a display of the device body 510. The device band 520 may have material that are semi-transparent or fully transparent to light emitted from the display such that displayed content may be visible to a user though the device band 520.

FIG. 6 illustrates a functional diagram of an exemplary device for use in mobile personal emergency response services, in accordance with one or more example embodiments of the present disclosure.

Referring to FIG. 6, the device 600 (e.g., similar to the wearable device 200 of FIG. 2) may include a device body 610 (e.g., having features of the device body 204 of FIG. 2) and a device band 620 (e.g., having features of the device band 202 of FIG. 2). The device band 620 is a closed band with an opening for containing the device body 610. The device body 610 may be inserted into the opening of the device band 620. A power charger 630 may operatively connect to the device body 610 without removing the devices body 610 from the device band 620.

FIG. 7A illustrates an exemplary device 700A for use in mobile personal emergency response services, in accordance with one or more example embodiments of the present disclosure.

Referring to FIG. 7A, the device 700A (e.g., similar to the wearable device 200 of FIG. 2) may include a device body 710A (e.g., having features of the device body 204 of FIG. 2) and a device band 720A (e.g., having features of the device band 202 of FIG. 2). The device band 720A may include one or more batteries (e.g., the one or more power sources 206 of FIG. 2) and one or more antennae (e.g., the one or more antennae 208 of FIG. 2). A cross section view 730 of the device band 720A, according to a cross section line 7B-7B, is shown in FIG. 7B.

FIG. 7B illustrates a cross-section 730 of the device band 720A of the device 700A of FIG. 7A, in accordance with one or more example embodiments of the present disclosure.

Referring to FIG. 7B, one or more layers (e.g., layers associated with an outer surface of the device band 720A) are not shown. The outer layers of the device band 720A may contain the layers shown in the cross-section 730. As shown, the one or more batteries and the one or more antennae of the device 700A may be layered within the device band 720A, with an antennae layer 732, a first intermediate layer 734 (e.g., a first shield layer having an intermediate material), a battery layer 736 (e.g., the first intermediate layer 734 may be a shield between the antenna layer 732 and the battery layer 736). A second intermediate layer 738 (e.g., a second shield layer having an intermediate material) may be opposite the first intermediate layer 734 to bookend the battery layer 736 and protect the battery layer 736. For example, the antenna layer 732 may be an embodiment of the one or more antennae 208 of FIG. 2, and the battery layer 736 may be an embodiment of the one or more power sources 206 of FIG. 2. The intermediate layers may reduce interference between the antennae layer 732 and the battery layer 736. The antenna layer 732 and the battery layer 736 may be arranged in a different order as long as they are separated by an intermediate layer (e.g., as shown in FIG. 7D). The antenna layer 732 may request and receive power signals to power the battery layer 736, which may power the device 700A (e.g., including the device body 710A, such as through the communication bus 210 of FIG. 2). The antenna layer 732 may be used to send wireless communications (e.g., the data 302 of FIG. 3, the one or more communications 304 of FIG. 3). The antenna layer 732 and the battery layer 736 may span the entire length of the device band 720A, or may span respective portions of the device band 720A. Alternatively, the antenna layer 732 and the battery layer 736 may be in separate portions of the device band 720A. The antenna layer 732 may correspond to the one or more antennae 208 of FIG. 2, and the battery layer 736 may correspond to the one or more power sources 206 of FIG. 2. The intermediate layers may be any protective layers and may have insulator properties. The intermediate layers may have the same or different thicknesses, and/or have the same or different materials.

FIG. 7C illustrates an exemplary device 700B for use in mobile personal emergency response services, in accordance with one or more example embodiments of the present disclosure.

Referring to FIG. 7C, the device 700B (e.g., similar to the wearable device 200 of FIG. 2) may include a device body 710B (e.g., having features of the device body 204 of FIG. 2) and a device band 720B (e.g., having features of the device band 202 of FIG. 2). The device band 720B may include one or more batteries (e.g., the one or more power sources 206 of FIG. 2) and one or more antennae (e.g., the one or more antennae 208 of FIG. 2). A cross section view 740 of the device band 720B, according to a cross section line 7D-7D, is shown in FIG. 7D.

FIG. 7D illustrates a cross-section 740 of the device band 720B of the device 700B of FIG. 7C, in accordance with one or more example embodiments of the present disclosure.

Referring to FIG. 7D, the cross-section 740 shows the layers of FIG. 7B, but in a different arrangement. The outer layers of the device band 720B may contain the layers shown in the cross-section 740. As shown, the second intermediate layer 738 may be arranged on the battery layer 736, which may be arranged on the first intermediate layer 734, which may be arranged on the antenna layer 732. The antenna layer 732 and the battery layer 736 may span the entire length of the device band 720B, or may span respective portions of the device band 720B. Alternatively, the antenna layer 732 and the battery layer 736 may be in separate portions of the device band 720B. The antenna layer 732 may correspond to the one or more antennae 208 of FIG. 2, and the battery layer 736 may correspond to the one or more power sources 206 of FIG. 2. The intermediate layers may be any protective layers and may have insulator properties. The intermediate layers may have the same or different thicknesses, and/or have the same or different materials.

It is understood that the above descriptions are for purposes of illustration and are not meant to be limiting.

Figure 8:
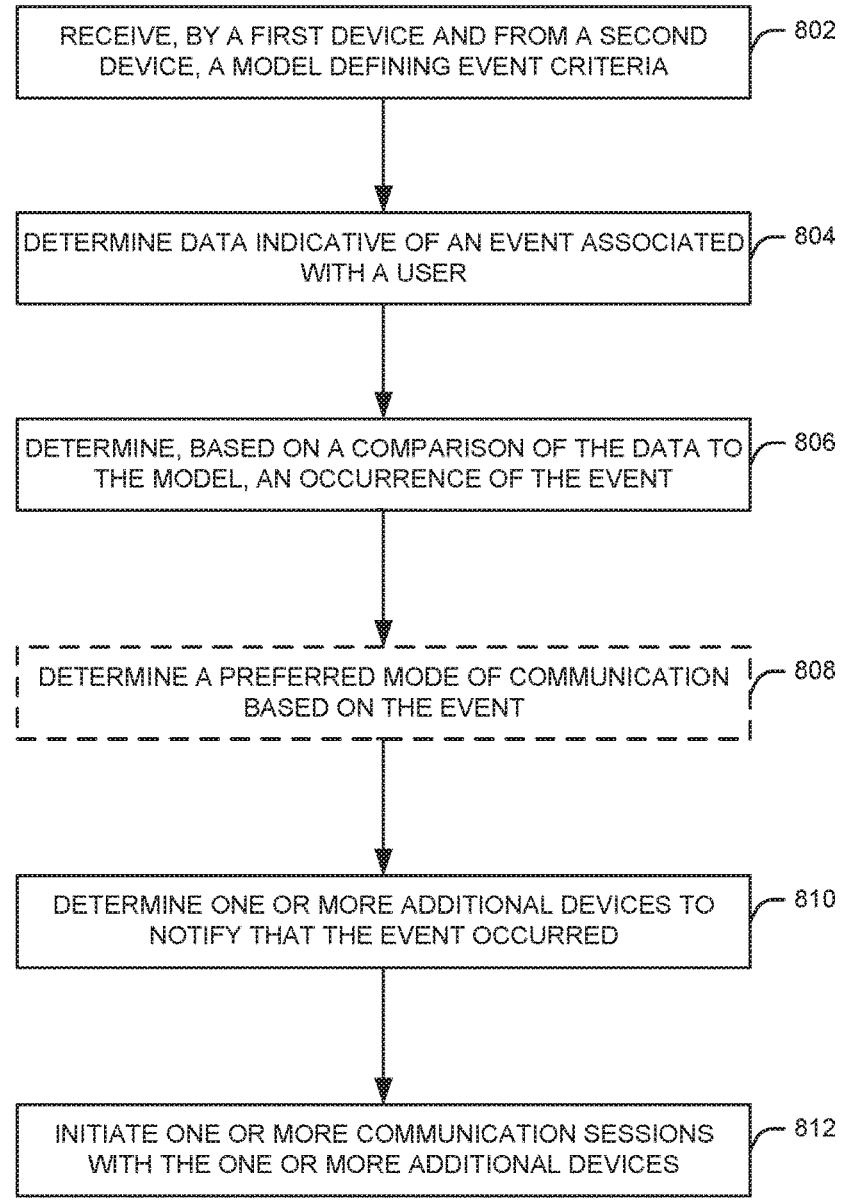
FIG. 8 illustrates a flow diagram of an illustrative process for enabling emergency response services, in accordance with one or more example embodiments of the present disclosure.

FIG. 8 illustrates a flow diagram of an illustrative process 800 for enabling emergency response services, in accordance with one or more example embodiments of the present disclosure.

At block 802, a device (e.g., the one or more devices 310 of FIG. 3) may receive an event detection model (e.g., the event detection model 330 of FIG. 3) from a second device (e.g., the remote computing server 320 of FIG. 3). For example, the device may be a wearable device (e.g., a watch device) and may receive a model from a remote computing server (e.g., a cloud-based computer/server, or a network-based on computer/server). The model may include an event criterion, such as data profiles (e.g., indicative of certain types of motion, electrocardiographs, etc.), thresholds/ranges respective to different biometric data (e.g., heart rate, blood pressure, blood glucose, respiration, blood oxygen, body temperatures, etc.). For example, the model may define thresholds used to determine when an event has occurred and merits an emergency service communication (e.g., a 9-1-1 call), and the criterion of the model may be customized based on user profile settings and/or historical data, and/or based on data of users with similar demographics (e.g., age, health profiles, etc.) as permitted and/or authorized by users. In some embodiments, thresholds indicating whether a person is experiencing an emergency event may be adjusted based on activities (e.g., exercising, sleeping, reading, outdoor activities, indoor activities, or the like) of a person over a period of time. In some embodiments, thresholds indicating whether a person is experiencing an emergency event may be adjusted based on surrounding environments (e.g., temperatures and/or humidity of surrounding environments). In some embodiments, the remote computing server may generate and update one or more machine learning models based on data (e.g., device motion data and/or biometric data) received from the wearable device (e.g., the data 302 of FIG. 3), and send the machine learning models to the wearable device.

At block 804, the device may determine data indicative of an event associated with a user. For example, the wearable device may include one or more sensors (e.g., sensors 218 in FIG. 2) to detect device data (e.g., accelerometer or other motion data) and biometric data (e.g., heart rate data, blood pressure data, blood glucose data, breathing data, etc.). The device may provide the data to the second device for generation of the event detection model. The device may compare detected motion and/or biometric data to the model to identify an event that may have occurred.

At block 806, the device may determine, based on a comparison of the data to the model, an occurrence of the event. For example, the wearable device may determine an occurrence of an emergency event based on a determination that a change of device data and/or biometric data deviates from/exceeds/fails to exceed a predetermined threshold. The wearable device may determine current data (e.g., current device data and/or biometric data) associated with a user wearing the wearable device. The wearable device may determine historic data (e.g., data obtained last time, average data of the historic data over a predetermined time period, or the like) associated with the user. The wearable device may determine one or more thresholds based on the user profile settings, the historic data, activities associated with the user, surrounding environments, or the like. The wearable device may determine a difference between the current data and historic data. The wearable device may determine that an emergency event occurs when the difference deviates from/exceeds/fails to exceed a predetermined threshold. For example, a motion data profile of the model may match the motion data determined at block 804, and may indicate falling event. Biometric data may be compared to criteria specific to the type of data. For example, heart rate data may be compared to one or more heart rate thresholds. Blood pressure data may be compared to one or more blood pressure thresholds, and so on. Based on device data and/or biometric data satisfying criteria of the model indicative of an event, the device may determine that the data of block 804 indicates that an event may have occurred, and the type of event (e.g., based on which type of data satisfies or matches event criteria defined by the model, which may define specific events corresponding to specific event criteria).

At block 808, the device may initiate, based on the occurrence of the event, a communication session with a third device. For example, the wearable device may initiate one or more communications, such as phone calls (e.g., using cellular or Wi-Fi), to one or more other devices, such as emergency call centers, medical professionals, family members, caregivers, and the like. For example, the device may have cellular and/or Wi-Fi communication capability to facilitate phone calls executed using the device (e.g., rather than relying on another device, such as a Bluetooth-paired device, to execute the phone call). The communication(s) initiated may be based on the type of event and/or user preferences. For example, a cardiac event or a falling event may trigger a phone call to an emergency service or call center. Some events may trigger a phone call or message to a caregiver or physician. The types of communications may be based on user preferences, user contact lists, and the like. The one or more communications may include information identifying the event, such as the type of event and/or data used to identify the event, allowing a receiving party of the one or more communications to respond appropriately.

Figure 9:
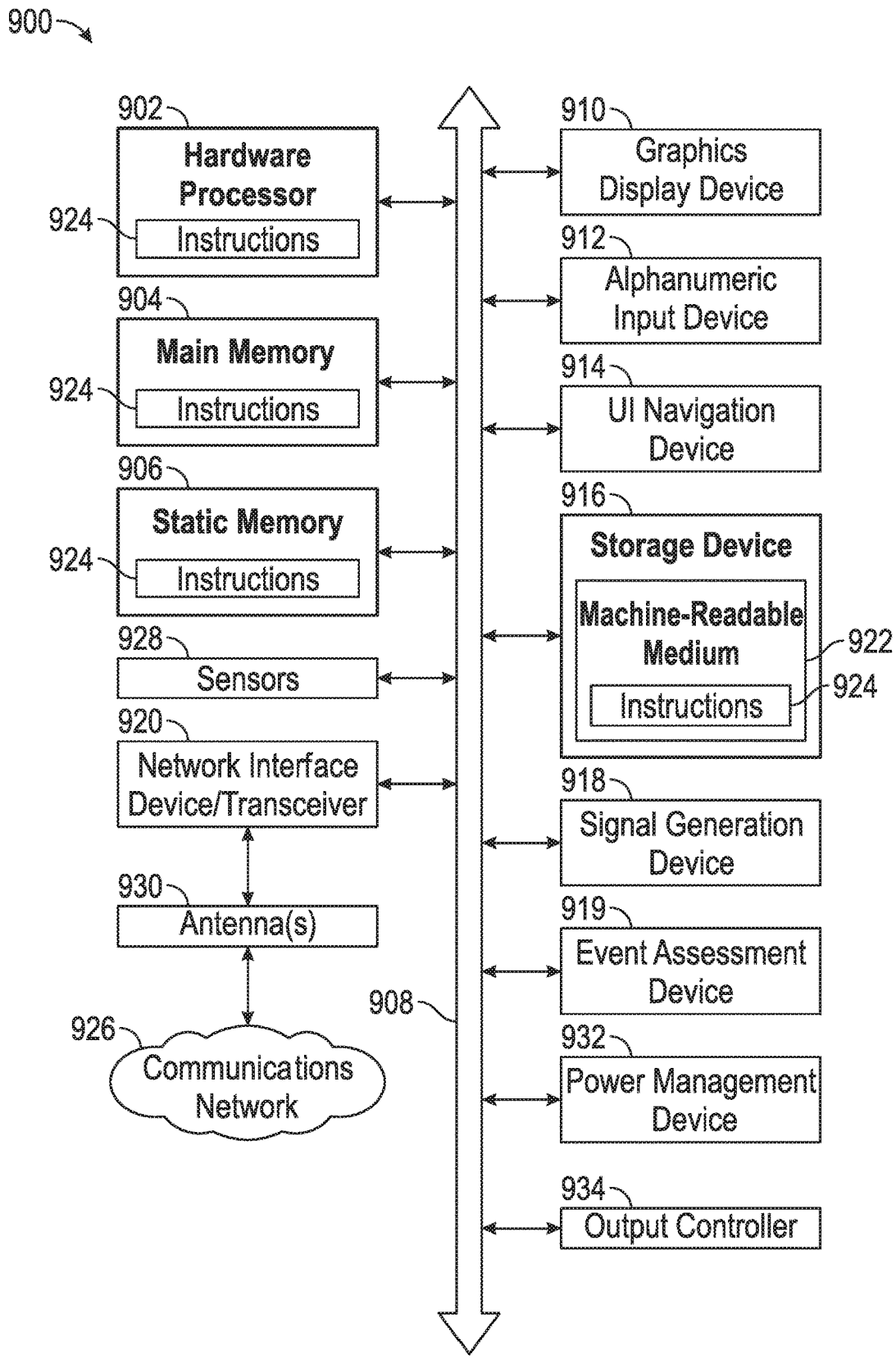
FIG. 9 illustrates a block diagram of an example of a machine, in accordance with one or more example embodiments of the present disclosure.

FIG. 9 illustrates a block diagram of an example of a machine 900 (e.g., the watch device 103 of FIG. 1, the wearable device 200 of FIG. 2, the one or more devices 310 of FIG. 3, the remote computing server 320 of FIG. 3, the one or more devices 308 of FIG. 4) or system upon which any one or more of the techniques (e.g., methodologies) discussed herein may be performed. In other embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in Wi-Fi direct, peer-to-peer (P2P) (or other distributed) network environments. The machine 900 may be a server, a personal computer (PC), a tablet PC, a set-top box (STB), a personal digital assistant (PDA), a mobile telephone, a wearable computer device, a web appliance, a network router, a switch or bridge, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a power management device 932, a graphics display device 910, an alphanumeric input device 912 (e.g., a keyboard), and a user interface (UI) navigation device 914 (e.g., a mouse). In an example, the graphics display device 910, alphanumeric input device 912, and UI navigation device 914 may be a touch screen display. The machine 900 may additionally include a storage device (i.e., drive unit) 916, a signal generation device 918 (e.g., an emitter, a speaker), an event assessment device 919 (e.g., similar to the event management module 312 of FIG. 3 and/or to the event/user management module 322 of FIG. 3), a network interface device/transceiver 920 coupled to antenna(s) 930, and one or more sensors 928, such as a global positioning system (GPS) sensor, a compass, an accelerometer, or other sensor. The machine 900 may include an output controller 934, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, etc.)).

The storage device 916 may include a machine readable medium 922 on which is stored one or more sets of data structures or instructions 924 (e.g., software) embodying or utilized by any one or more of the techniques or functions described herein. The instructions 924 may also reside, completely or at least partially, within the main memory 704, within the static memory 906, or within the hardware processor 902 during execution thereof by the machine 900. In an example, one or any combination of the hardware processor 902, the main memory 904, the static memory 906, or the storage device 916 may constitute machine-readable media.

The event assessment device 919 may carry out or perform any of the operations and processes (e.g., process 800 of FIG. 8) described above. The event assessment device 919 may be included in the wearable device 200 of FIG. 2.

While the machine-readable medium 922 is illustrated as a single medium, the term "machine-readable medium" may include a single medium or multiple media (e.g., a centralized or distributed database, and/or associated caches and servers) configured to store the one or more instructions 924.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 900 and that cause the machine 900 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 924 may further be transmitted or received over a communications network 926 using a transmission medium via the network interface device/transceiver 920 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 920 may include one or more physical jacks (e.g., Ethernet, coaxial, or phone jacks) or one or more antennas to connect to the communications network 926. In an example, the network interface device/transceiver 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 900 and includes digital or analog communications signals or other intangible media to facilitate communication of such software.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device," "user device," "communication station," "station," "handheld device," "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating," when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A method, comprising:
    receiving, by at least one processor of a first device, a model from a second device, the model comprising an event criterion, wherein the first device is a wearable device, and wherein the model is based on first data previously sent from the first device to the second device, the first data associated with a user;
    determining, by the at least one processor, second data indicative of an event associated with the user;
    determining, by the at least one processor, based on a comparison of the second data to the model, an occurrence of the event; and
    initiating, by the at least one processor, based on the occurrence of the event, a communication session with a third device.

2. The method of claim 1, wherein the event is a first event, wherein the model is a first model, wherein the event criterion is a first event criterion, and wherein the communication session is a first communication session, the method further comprising:
    sending the second data and an indication of the first event to the second device;
    receiving a second model from the second device, wherein the second model comprises a second event criterion different than the first event criterion, and wherein the second event criterion are based on the second data and the indication of the first event;
    determining third data indicative of a second event associated with the user;
    determining, based on a comparison of the third data to the second model, an occurrence of the second event; and
    initiating, based on the occurrence of the second event, a second communication session.

3. The method of claim 1, further comprising:
    determining, based on the second data and the model, an event type associated with the event; and
    sending an indication of the event type to the third device.

4. The method of claim 1, wherein the event is associated with a user falling, and wherein the second data comprises motion data associated with one or more accelerometers of the first device.

5. The method of claim 1, wherein the event is associated with a cardiac event, and wherein the second data comprises biometric data associated with a user wearing the first device.

6. The method of claim 1, wherein the event criterion comprises one or more thresholds based on at least one of a user profile associated with a user wearing the first device, activities performed by the user over a period of time, a surrounding environment associated with the first device, or historic data associated with the user, the historic data comprising the first data.

7. The method of claim 1, further comprising:
    receiving, from the third device, a query associated with confirming the occurrence of the event;
    receiving a user input indicative of the confirmation; and
    sending, to the third device, an indication of the confirmation.

8. The method of claim 1, wherein the first device comprises a wearable band, the wearable band comprising a power source, the method further comprising receiving power from the power source.

9. The method of claim 8, wherein the wearable band further comprises an antenna, wherein the communication session is initiated using the antenna.

10. The method of claim 9, wherein the wearable band further comprises an intermediate material between the antenna and the power source.

11. The method of claim 1, further comprising:
    determining a user preference associated with the event and the third device,
    wherein initiating the communication session with the third device is based on the user preference.

12. The method of claim 1, further comprising:
    determining, based on the model, that the event is associated with an event type,
    wherein initiating the communication session with the third device is based on the event type.

13. The method of claim 1, wherein the communication session is a first communication session, the method further comprising:
    initiating a second communication session with a fourth device based on the occurrence of the event.

14. A wearable apparatus comprising:
    a band comprising a power source; and
    processing circuitry coupled to the power source and to memory, the processing circuitry configured to:
        receive, from a first device, a model comprising event criteria, wherein the model is based on first data previously sent from the wearable apparatus to the first device, the first data associated with a user;
        determine second data indicative of an event associated with the user;
        determine, based on a comparison of the second data to the model, an occurrence of the event; and
        initiating, based on the occurrence of the event, a communication session with a second device.

15. The wearable apparatus of claim 14, wherein the wearable apparatus is geographically remote from the first device.

16. The wearable apparatus of claim 14, wherein the communication session comprises a cellular telecommunication.

17. The wearable apparatus of claim 14, wherein the band further comprises an antenna.

18. A system, comprising:
    a band comprising a power source; and
    processing circuitry coupled to the power source and to memory, the processing circuitry configured to:
        receive, from a first device, a model comprising event criteria, wherein the model is based on first data previously sent from the system to the first device, the first data associated with a user;
        determine second data indicative of an event associated with the user;
        determine, based on a comparison of the second data to the model, an occurrence of the event; and
        initiating, based on the occurrence of the event, a communication session with a second device.

19. The system of claim 18, wherein the system is geographically remote from the first device.

20. The system of claim 18, wherein the band further comprises an antenna.

\* \* \* \* \*